United States Patent
Muesch et al.

(10) Patent No.: US 9,219,785 B2
(45) Date of Patent: Dec. 22, 2015

(54) METHOD AND UNIT FOR THE RELIABLE ALLOCATION OF NETWORK ELEMENTS TO A WIRELESS SENSOR NETWORK

(75) Inventors: Guido Muesch, Linnich (DE); Karin Klabunde, Bochum (DE); Heribert Baldus, Aachen (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 2145 days.

(21) Appl. No.: 10/552,646

(22) PCT Filed: Mar. 30, 2004

(86) PCT No.: PCT/IB2004/001037
§ 371 (c)(1),
(2), (4) Date: Jul. 18, 2006

(87) PCT Pub. No.: WO2004/089201
PCT Pub. Date: Oct. 21, 2004

(65) Prior Publication Data
US 2006/0270344 A1  Nov. 30, 2006

(30) Foreign Application Priority Data
Apr. 10, 2003 (EP) .................... 031009657

(51) Int. Cl.
H04W 4/00 (2009.01)
H04L 29/08 (2006.01)
G06F 19/00 (2011.01)
H04W 8/26 (2009.01)
H04W 12/06 (2009.01)
H04W 84/18 (2009.01)
A61B 5/00 (2006.01)

(52) U.S. Cl.
CPC .................. *H04L 67/12* (2013.01); *A61B 5/002* (2013.01); *A61B 2562/08* (2013.01); *G06F 19/3418* (2013.01); *H04L 67/16* (2013.01); *H04W 8/26* (2013.01); *H04W 12/06* (2013.01); *H04W 84/18* (2013.01)

(58) Field of Classification Search
USPC .................. 600/300; 340/825; 455/432.1, 450
See application file for complete search history.

(56) References Cited

U.S. PATENT DOCUMENTS

| | | | | |
|---|---|---|---|---|
| 4,641,373 A | * | 2/1987 | Shutterly ........................ | 398/62 |
| 5,307,297 A | * | 4/1994 | Iguchi et al. .................. | 345/169 |
| 5,383,044 A | * | 1/1995 | Borchardt et al. ............ | 398/111 |
| 5,385,297 A | * | 1/1995 | Rein et al. .................... | 236/49.3 |
| 5,442,341 A | * | 8/1995 | Lambropoulos ............. | 340/5.26 |
| 5,936,539 A | | 8/1999 | Fuchs | |

(Continued)

FOREIGN PATENT DOCUMENTS

| WO | WO 01/26335 A2 | 4/2001 |
|---|---|---|
| WO | WO 02/30140 A2 | 4/2002 |
| WO | WO 02/058327 A2 | 7/2002 |

*Primary Examiner* — Suhail Khan

(57) ABSTRACT

The reliable and controlled allocation of network elements particularly medical sensors (2) to a network (4) without prior configuration of the wireless sensors or of the network administration system can be carried out using an allocation unit (1) for allocating network elements (2) to a wireless network (4), which allocation unit (1) comprises a transmitter which transmits, in a user-controlled manner, a code to a first network element (2), which code causes the first network element (2) to transmit its ID together with the code (encoded ID) so that the latter can be received by a second network element (3) which allocates the first network element (2) to its network (4).

14 Claims, 3 Drawing Sheets

(56) References Cited

U.S. PATENT DOCUMENTS

| | | | | |
|---|---|---|---|---|
| 5,974,032 | A * | 10/1999 | Snowden et al. | 370/316 |
| 6,021,123 | A * | 2/2000 | Mimura | 370/331 |
| 6,215,396 | B1 * | 4/2001 | Script | 340/545.1 |
| 6,238,338 | B1 * | 5/2001 | DeLuca et al. | 600/300 |
| 6,442,150 | B1 * | 8/2002 | Kondo et al. | 370/331 |
| 7,469,125 | B2 * | 12/2008 | Nurmi | 455/11.1 |
| 2001/0023315 | A1 | 9/2001 | Flach et al. | |
| 2002/0013538 | A1 * | 1/2002 | Teller | 600/549 |
| 2002/0109621 | A1 * | 8/2002 | Khair et al. | 341/174 |
| 2002/0180622 | A1 * | 12/2002 | Lui et al. | 341/22 |
| 2003/0016122 | A1 * | 1/2003 | Petrick | 340/10.41 |
| 2004/0049451 | A1 * | 3/2004 | Berardi et al. | 705/39 |
| 2004/0068756 | A1 * | 4/2004 | Chiu | 725/135 |
| 2004/0155809 | A1 * | 8/2004 | Eyer | 341/176 |
| 2004/0172535 | A1 * | 9/2004 | Jakobsson et al. | 713/168 |

\* cited by examiner

METHOD AND UNIT FOR THE RELIABLE ALLOCATION OF NETWORK ELEMENTS TO A WIRELESS SENSOR NETWORK

The present invention relates to a method and a unit for the reliable allocation of new network elements to a wireless network.

A preferred field of application is the field of monitoring patients by means of medical sensors which are connected to a wireless network. In this case, a new network element (e.g. a medical sensor which monitors the blood pressure of a patient) must be allocated to an existing network (e.g. the patient's other sensors, which monitor the temperature of the patient for example) in a reliable and unambiguous manner in order to prevent incorrect configurations. In the medical sector, this is often made more difficult by the fact that the staff have to operate under a high time pressure and high mental and physical stress. Moreover, in a sector such as this allocation errors must not occur. It is obvious that a reliable and unambiguous allocation of network elements to a network is absolutely necessary in this case.

Within the context of the present invention, medical sensors are sensors which record data from a patient and forward it to a processing unit. Within the context of the present invention, the term "patient data" includes both physiological data, such as real time ECG signals, blood pressure, $CO_2$ saturation in the blood, blood sugar level, temperature, etc., and also non-physiological data, such as battery power, patient location, etc.

U.S. patent application US2001/0023315 A1 discloses a medical system in which sensors transmit patient data to radio frequency transceivers which are mounted on the ceiling. These transceivers transmit the data to an LAN, with each sensor transmitting to at least two transceivers and the better connection being used. However, the configuration of the sensors and their incorporation into the LAN also in this case has to be carried out manually, and thus in a time-consuming and complicated manner. Furthermore, US patent application US2002/109621 A1 describes protocols for use in a monitoring system comprising wireless biosensors, but in this case too the initial allocation of sensors to the system has to be carried out manually.

It is an object of the present invention to provide a method and a unit which allow the reliable and controlled allocation of network elements (particularly medical sensors) to a network with prior configuration of the wireless sensors or of the network administration system.

It has now been found that the use of an allocation unit which transmits codes and hence brings about the transmission of encoded IDs meets the necessary profile of requirements.

One object of the present invention is a method of allocating network elements to a wireless network, wherein an allocation unit (ZG) transmits a code to a first network element (NE-1), which code causes the first network element (NE-1) to transmit its ID together with the code (encoded ID) so that the latter can be received by a second network element (NE-2) which allocates the first network element (NE-1) to its network.

In the method according to the invention, either the ID of the device (network element) that is to be incorporated is passed to the existing network or the existing network and the new device that is to be incorporated are brought into connection by a common code.

Figure 1:
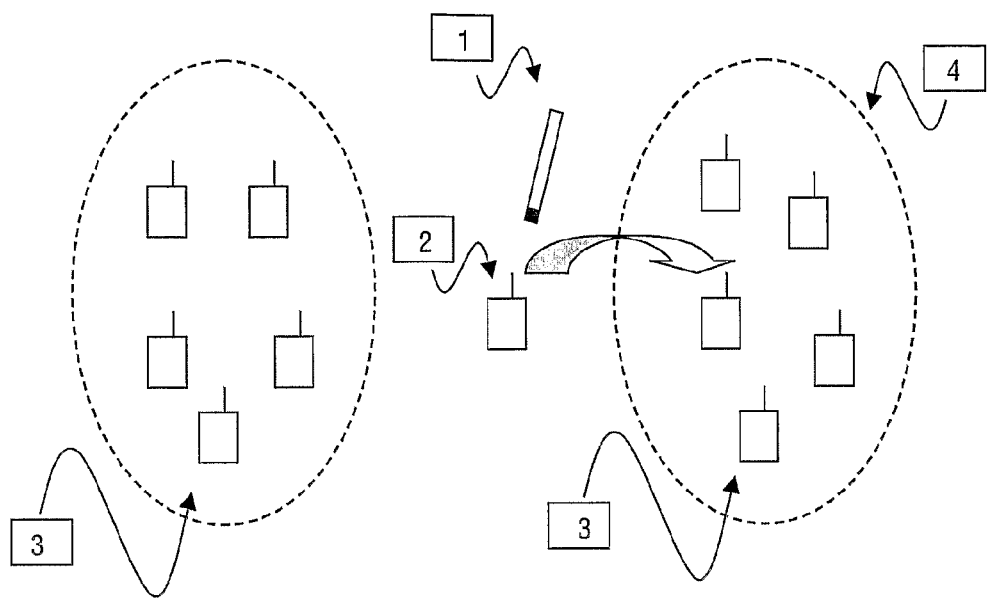
FIG. 1 shows, schematically, a method according to an embodiment of the invention.

The method according to the invention is shown schematically in FIG. 1: a network 4 is built up around a network element with network administration function 3. An allocation unit 1 incorporates, into the network 4 around the network element with network administration function 3, a network element 2 that is to be allocated.

Figure 2:
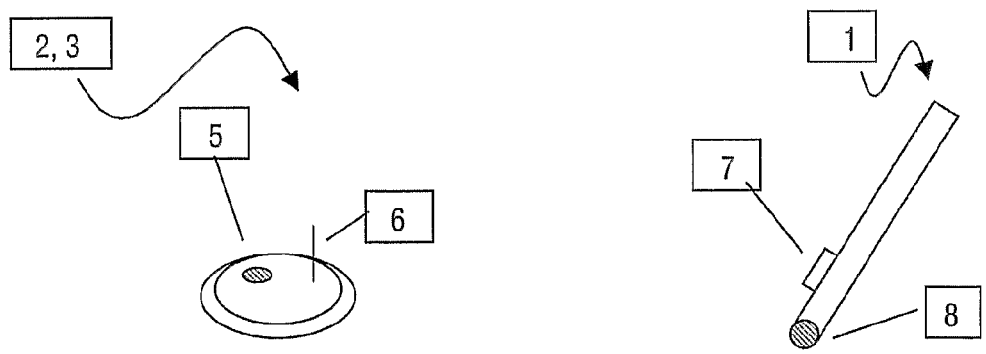
FIG. 2 shows components used for a method according to an embodiment of the invention.

The components used for the method according to the invention are shown in FIG. 2. A network element 2 and a network element with network administration function 3 comprise a receiver 5 and a radio interface 6. An allocation unit 1 has a transmitter 8 which can be activated for example by a push button 7.

The advantages of the method according to the invention are in particular that no manual presetting of the network elements or network is required. The method according to the invention allows intuitive operation by non-technical staff and provides the possibility of direct feedback about successful performance of the operation by means of LEDs on the network elements. It allows reliable allocation of wireless sensors/network elements even in environments in which a number of wireless networks of the same type are used next to one another.

The transmission of the code by the allocation unit may take place in various ways; one possibility for carrying out the method according to the invention consists in the allocation unit transmitting an encoded light pulse.

In this variant of the method, the allocation unit transmits a light pulse which is used to send out a code that is unique for each allocation unit. The sending of the encoded light pulse preferably takes place in a user-activated manner, for example by pressing once or holding down a button on the allocation unit.

By receiving the code from the allocation unit, a network element that has a receiver for optical pulses is caused to transmit, for a given time period, its identification (ID) together with the received code. This operating state of the network element may be displayed optically for example with the aid of an LED. An LED can also display the reception of the light pulse from the allocation unit.

The ID transmitted by NE-1 together with the code received from the allocation unit (hereinafter referred to as the "encoded ID") may then be received by a network element NE-2, which is authorized to allocate new network elements to the network. The network element NE-2 is advantageously activated only temporarily to receive encoded IDs, see below.

By using differently encoded allocation units, it can be ensured that in two adjacent networks located within range, devices can be unambiguously allocated to a network.

Figure 3:
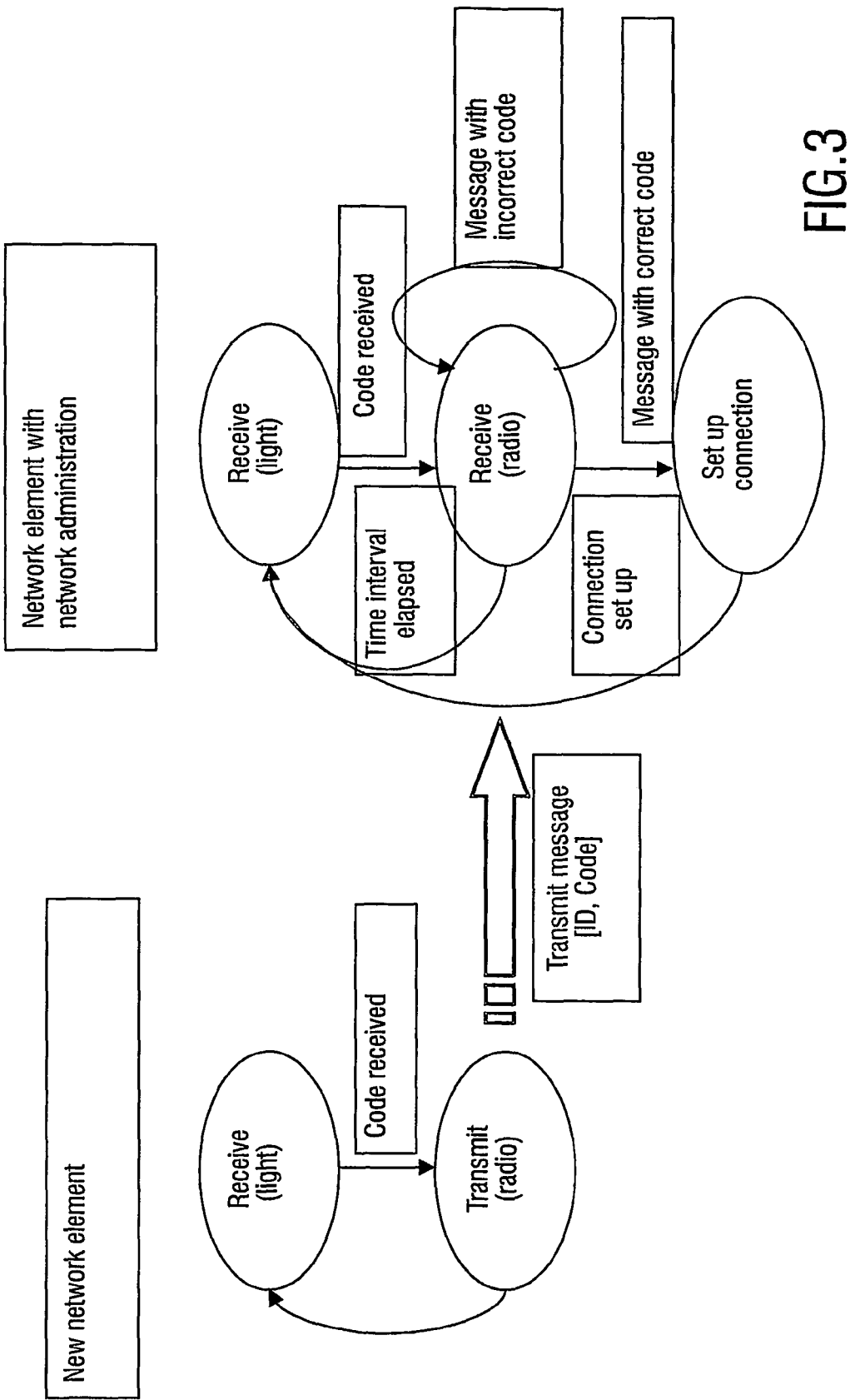
FIG. 3 shows a procedure of an allocation by an encoded light pulse according to an embodidment of the invention.

One preferred procedure of an allocation according to the invention by means of an encoded light pulse is shown in FIG. 3. In FIG. 3, two network elements—a first network element NE-1 which is to be newly allocated to a network (new network element) and a second network element NE-2 which includes a network administration function (network element with network administration)—are in the "Receive (light)" state for receiving encoded light pulses from an allocation unit (ZG). If a code from ZG is received at NE-1, then NE-1 switches into the "Transmit (radio)" state. In this case, messages having their own identification and the received code (so-called encoded IDs) are transmitted by NE-1 regularly over a defined time interval.

The time interval within which NE-1 transmits encoded IDs preferably lies in the range from one second to one minute, particularly preferably in the range from two seconds to half a minute and in particular in the range from five to ten seconds. The repetition rate within this time interval, that is to say the time after which the signal (the encoded ID) is again transmitted, preferably lies in the range from 0.05 to 5 seconds, particularly preferably in the range from 0.1 to 3 seconds and in particular in the range from 0.2 to 1 second. Accordingly, the frequency with which an NE-1 activated by ZG transmits its encoded ID may preferably be from a few times to a few hundred times, for example one, two, three, four, five, six, seven, eight, nine or ten times to fifty or a hundred times or more. The choice of time window within which two network elements come into contact forms a compromise between a reaction that is as short as possible, in order to be able to give the user rapid feedback, and a power consumption that is as low as possible, said power consumption increasing with the number of transmission operations. Values which have proven useful in practice are, for example, a time window of from 5 to 10 seconds at a transmission rate of 2 to 4 packets per second, resulting in a frequency of 10 to 40 times per second. In the case of smaller time windows, the intervals should be chosen to be shorter; in the case of long time windows they should be chosen to be longer.

As shown in FIG. 3, the network element NE-2 with network administration function can switch into the "Set up connection" state when it receives an encoded ID. By contrast, if the network element with network administration function receives a message with an unsuitable, that is to say incorrect, code, it remains in the "Receive (radio)" state. After the time interval has elapsed, it then switches back into the "Receive (light)" state. One disadvantage of this variant is that NE-2 must already know the code, that is to say each individual network to which new elements are to be allocated must have its own network element with network administration function.

According to the invention, this is advantageously effected in that the allocation unit is likewise used to activate the network element with network administration function. Following appropriate activation, the network element with network administration function is ready to receive encoded IDs from network elements activated beforehand by ZG. Other messages relating to the connection setup are ignored during this time, so that unambiguous allocation is ensured.

In particularly preferred methods according to the invention, the activation of NE-2 to receive the encoded ID from NE-1 takes place by receiving the code from the allocation unit.

In this preferred variant of the method according to the invention, a network element NE-2 has network administration properties, it being possible for the network around NE-2 to have further network elements NE-x. In a network element NE-1 that is to be allocated to the network around NE-2, an event E1 is brought about by means of the allocation unit (NE-1 is caused to transmit its encoded ID). At the same time as this event E1, an event E2 is brought about in the network element NE-2 (NE-2 is caused to receive encoded IDs). Only when NE-2 receives at around the same time a request to set up a connection is this request answered with a positive response. In this context "at around the same time" means that the reception must lie within a time window following the event E2. For this purpose, NE-1 preferably sends its request periodically within a time period following the event E1 (see below). The two time periods of NE-1 and NE-2 must overlap for there to be a successful connection setup.

In this variant, only the temporal proximity of the events (activation by allocation unit) is used in order that only the respectively activated network elements NE-1 and NE-2 set up a connection with one another. In the hospital environment, it may be possible that two adjacent networks that are within range are activated at the same time. In order still to ensure an unambiguous allocation in this case, the events E1 and E2 may receive a unique ID. NE-1 then transmits its request together with the received ID and NE-2 only accepts requests with the received ID. The allocation unit may make use of various technologies which allow short-range data transmission, in particular wireless technologies such as, for example, Near Field Communication, for instance RF-ID, or preferably infrared communication (see above).

In this preferred variant of the method according to the invention, the authority of the network which performs the allocation of new network elements to the network (network administration) is likewise activated by the signal of the allocation unit (encoded light pulse or radio signal) in order to react, for a defined time period, to transmitted identifications from new network elements so as then to allocate them to the network. Only identifications from new network elements which have received the same code via the allocation unit are accepted.

The preferred procedure described above is hence supplemented by the following steps: if the network element with network administration NE-2 receives an encoded light pulse from the allocation unit, then it switches from the "Receive (light)" state to the "Receive (radio)" state. It now accepts only messages having the same code as was given by ZG to NE-2. If no valid message is received within a defined time period, NE-2 switches back to the "Receive (light)" state. If a valid message, that is to say an ID encoded with the same code, is received, there is a transition to the "Set up connection" state. Following this state, there is a switch back to the "Receive (light)" state in order to be able to integrate further network elements into the network.

In this case, too, the time interval within which NE-2 can receive encoded IDs preferably lies in the range from one second to one minute, particularly preferably in the range from two seconds to half a minute and in particular in the range from five to ten seconds.

In wireless networks without central network administration, the two functions "Receive (light)→Transmit (radio)" and "Receive (light)→Receive (radio)" may be implemented in each individual network element; in this way an allocation between any desired network elements can be produced.

In order to make the method more user-friendly, the respective operating states of the individual network elements may be made to be optically or acoustically perceptible. Thus, for example, a flashing LED on the unit may indicate the state "Transmit (radio)", and an LED that stays lit for longer (for example 2 seconds) could indicate that allocation has been successful.

In addition, the network elements may be given a network checking function. The activation of the network element, that is to say the reception of an encoded light pulse, leads to an optical report of all network elements located in the wireless network. Thus the affiliation of individual network elements in the network can be rapidly checked.

The method according to the invention has the advantage that the sequence in which the network element with network function and a network element that is to be newly allocated are activated is of no significance. Moreover, an unambiguous allocation is ensured by a unique code for each allocation unit. If in the procedure according to the invention the network elements are provided with LEDs, for example, then optical reports brought about by ZG allow a rapid diagnosis of the allocation of network elements to the network.

As an alternative to activation by means of an encoded light pulse, it is also possible to use for the method according to the invention allocation units which activate the network elements by means of a radio signal. In one preferred variant of the method according to the invention, the allocation unit transmits an encoded radio signal.

This variant is entirely analogous to the variant described above, apart from the fact that in this case the allocation unit does not transmit an encoded light pulse but rather an encoded radio signal. The allocation unit therefore requires a radio interface (transmitter). In this variant, the optical transmission of the unique code is thus replaced by the use of the radio interface already present on the network element.

In this variant, the allocation unit should have a short transmission range in order that only the desired device is selected. In this variant the allocation unit preferably has a range of from 0.5 to 150 cm, particularly preferably 1 to 100 cm and in particular 2 to 20 cm.

One preferred procedure for an allocation by means of an encoded radio signal according to the invention is described below. Two network elements, a first network element NE-1 which is to be newly allocated to a network and a second network element NE-2 which includes a network administration function, are in the "Receive (radio, code)" state for receiving encoded radio signals from an allocation unit (ZG). If a code from ZG is received at NE-1, then NE-1 switches into the "Transmit (radio, encoded ID)" state. In this case, messages having their own identification and the received code (so-called encoded IDs) are transmitted by NE-1 regularly over a defined time interval.

The time interval within which NE-1 transmits encoded IDs preferably lies in the range from one second to one minute, particularly preferably in the range from two seconds to half a minute and in particular in the range from five to ten seconds. The repetition rate within this time interval, that is to say the time after which the signal (the encoded ID) is again transmitted, preferably lies in the range from 0.05 to 5 seconds, particularly preferably in the range from 0.1 to 3 seconds and in particular in the range from 0.2 to 1 second. Accordingly, the frequency with which an NE-1 activated by ZG transmits its encoded ID may be from a few times to a few hundred times.

When the network element NE-2 with network administration function receives an encoded ID, it can thus switch into the "Set up connection" state. As an alternative and preferably, it is also possible—as described above—for the allocation unit to likewise be used to activate the network element with network administration function. Following appropriate activation by the radio signal from ZG, the network element with network administration function is ready to receive encoded IDs from network elements activated beforehand by ZG. Other messages are ignored during this time, so that unambiguous allocation is ensured.

The procedure shown in FIG. 3 and described above is hence supplemented by the following steps: if the network element with network administration NE-2 receives an encoded radio signal from the allocation unit, then it switches from the "Receive (radio, code)" state to the "Receive (radio, encoded ID)" state. It now accepts only messages having the same code as was given by ZG to NE-2. If no valid message is received within a defined time period, NE-2 switches back to the "Receive (radio, code)" state. If a valid message, that is to say an ID encoded with the same code, is received, there is a transition to the "Set up connection" state. Following this state, there is a switch back to the "Receive (radio, code)" state in order to be able to integrate further network elements into the network.

In this variant, too, in wireless networks without central network administration the two functions "Receive (radio, code)→Transmit (radio, encoded ID)" and "Receive (radio, code)→Receive (radio, encoded ID)" may be implemented in each individual network element; in this way an allocation between any desired network elements can be produced.

In the method variants described above, the network element that is to be allocated transmits its encoded ID to the network element with network administration function. However, the method according to the invention may also be configured such that the network element that is to be allocated is activated by the reception of the code, transmits its encoded ID and this encoded ID is transmitted not to NE-2 but rather to the allocation unit. The allocation unit can then forward the received encoded ID to the network element with network administration function and at the same time acts as a conveyor of the encoded ID without NE-1 and NE-2 having to communicate directly with one another.

In a preferred variant of the method according to the invention, the allocation unit may receive the encoded ID from NE-1 and transmit it to NE-2.

Figure 4:
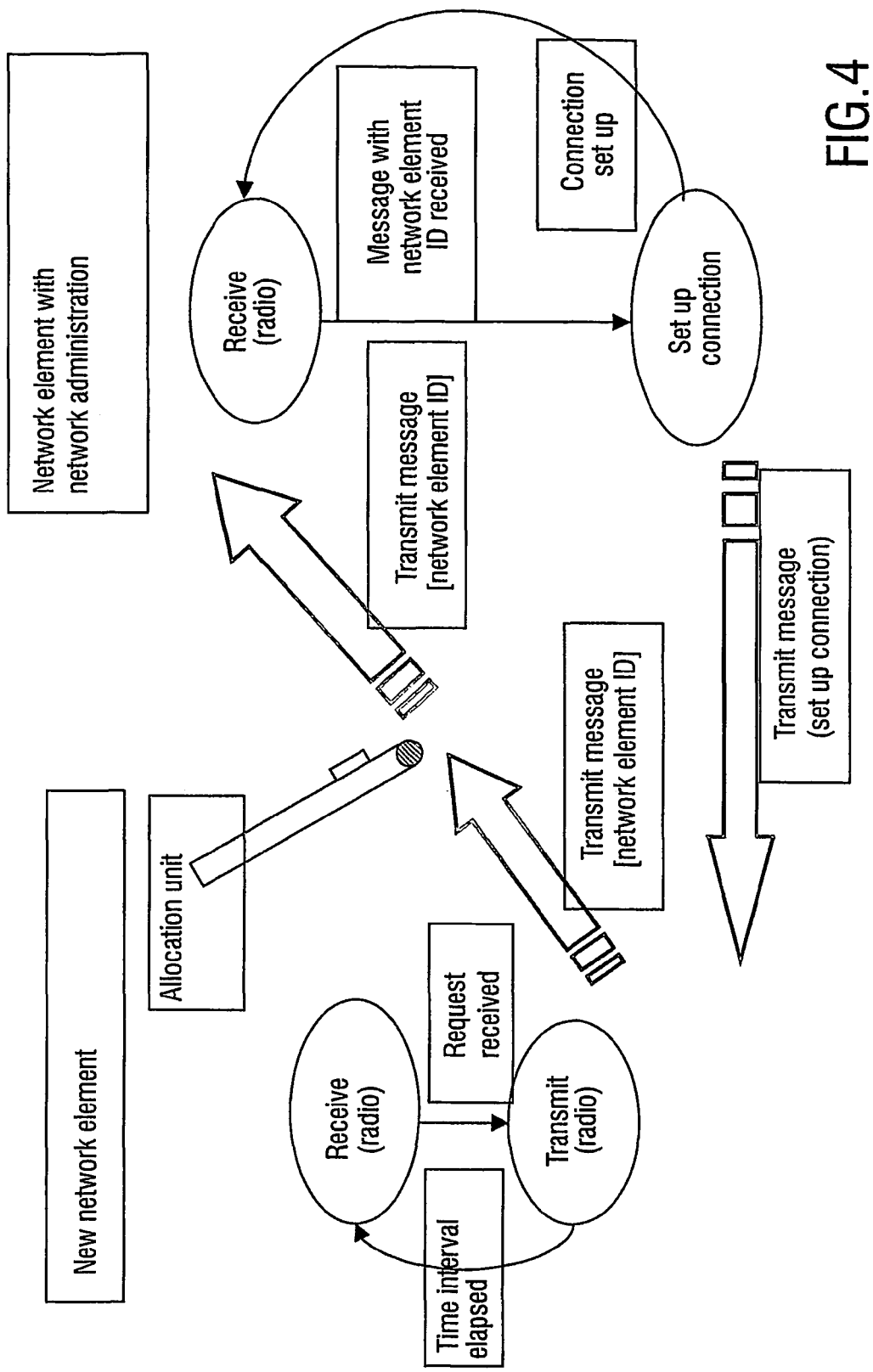
FIG. 4 shows a procedure of an allocation according to an embodiment of the invention.

Such a preferred procedure is shown in FIG. 4. The allocation unit is in this case configured such that it has the same network interface as that used in the wireless network. If the allocation unit (for example a ZG with radio interface, see above) comes close enough to the new network element NE-1, then a protocol is brought about by means of which the allocation unit picks up the unique identification of the new network element. The allocation unit then has network authority, in which the identification (encoded ID) is output again and the network element NE-1 is made known to the network. The concept of coming closer to a defined distance is achieved either by a threshold value in the received signal strength or by a very low transmission power of the ZG or by a combination of these two measures.

The incorporation of new network elements by means of the allocation unit according to the method variant described above may be further refined by incorporating a "pick-up" function for example. In this case, the pick-up of the new network element is not brought about by bringing the allocation unit closer but rather by pressing a button for example. If the user holds the button down, as may be indicated for example by an LED, then the ZG receives the identifier. In order to output the encoded ID to a further network element (with network administration function), the button must simply be released, and this may again be shown by an LED or by an LED going out.

As already described above, the direction of allocation may be chosen at will, that is to say it is possible either to transmit the identification of the new network element to a network administration element or to transmit the network identification of the network element with network administration function to the network element that is to be newly incorporated. Of course, bidirectional transmission is also possible if a flexible use of the two allocation paths is desired.

The method according to the invention can also be expanded to the extent that network elements can be removed from the network by means of the allocation unit. A preferred variant of the method according to the invention provides that the allocation unit can transmit a second code which causes a first network element (NE-1) to leave the network of the second network element (NE-2).

In cases in which the entire network is to be broken up, it may be complicated to cause each network element to leave the network. As an alternative to this, it is possible to cause the network element with network administration function to break up the network. In this case, only one command is required to remove all network elements from the network. In further preferred methods, the allocation unit can transmit a second code which causes the second network element (NE-2) with network administration function to break up the network.

For the second code, the allocation unit may be provided with a further push button which is actuated for the transmission of the "Leave" or "Break-up" code. However, it is also possible to carry out the abovementioned variants of the method with the code that is already present in the allocation unit. This has the advantage of a simpler design of the allocation unit and lower susceptibility to operating errors.

In such variants of the method, the difference between the "Leave" or "Break-up" code and the first code may be that the code is transmitted over a longer time period or a number of times in succession. In the first case, time periods of around 2 seconds have proved useful; in the second case it has proved useful for the first code to be sent twice by means of a double click. In summary, methods according to the invention are also preferred in which the second code for removing network elements or for breaking up the network consists in the first code being transmitted over a longer time period or a number of times.

Another object of the invention is an allocation unit for allocating network elements to a wireless network, comprising a transmitter which transmits, in a user-controlled manner, a code to a first network element (NE-1), which code causes the first network element (NE-1) to transmit its ID together with the code (encoded ID) so that the latter can be received by a second network element (NE-2) which allocates the first network element (NE-1) to its network.

The allocation unit according to the invention may be configured such that it transmits the code as an encoded light signal (light pulse), as an encoded radio signal or in some other way to the network elements. Preferred allocation units according to the invention comprise as transmitter a device for transmitting an encoded light pulse and/or an encoded radio signal.

As described in detail above, it is advantageous if the allocation unit does not only activate the network element that is to be newly incorporated in order to transmit, but also the network administration element in order to receive specific messages. In this case, allocation units according to the invention are preferred in which the code which causes the first network element (NE-1) to transmit its ID together with the code (encoded ID) causes the second network element (NE-2) to be ready to receive the encoded ID from NE-1.

Allocation units which can transmit an encoded ID are particularly advantageous. Such allocation units additionally comprise a receiver for receiving encoded IDs.

The respective operating states of the network elements and of the allocation unit are preferably displayed in a user-friendly manner, it being possible for both optical and acoustic signals to be used. Allocation units according to the invention which additionally comprise one or more devices for displaying the respective operating state are particularly preferred.

The display devices are preferably optical devices since acoustic signals from the surroundings may be regarded as disruptive. Thus it is possible for example for colored light-emitting diodes (LEDs) or liquid crystal displays (LCDs) to be used to display operating states of the allocation unit.

In order to carry out the preferred variants of the method with a "Leave" or "Break-up" function, the allocation unit according to the invention may additionally be provided with a transmitter which transmits, in a user-controlled manner, a second code which causes the first network element (NE-1) to leave the network of the second network element (NE-2) or causes the second network element (NE-2) with network administration function to break up the network.

LIST OF REFERENCES 1 allocation unit
2 network element that is to be allocated NE-1
3 network element with network administration function NE-2
4 network
5 receiver
6 radio interface
7 push button
8 transmitter

The invention claimed is:

1. A method of allocating network elements to a wireless network, wherein
with a transmitter of an allocation unit, transmitting in a user-controlled manner, a first code to a first network element, which first code causes the first network element to transmit an encoded identification (ID) comprising its ID and the received first code, so that the encoded ID is received by a second network element having network administration function, which allocates the first network element to its wireless network,
wherein a temporary activation of the second network element to receive the encoded ID from the first network element takes place by receiving the first code from the allocation unit,
wherein the second network element accepts only identifications from network elements having the same first code, and
wherein the allocation unit is one of a plurality of differently encoded allocation units, said allocation unit having a short transmission range and the transmitted first code is unique for each allocation unit.

2. The method as claimed in claim 1, wherein the allocation unit transmits an encoded light pulse.

3. The method as claimed in claim 1, wherein the allocation unit transmits an encoded radio signal.

4. The method as claimed in claim 2, further including:
in response to receiving the code from the allocation unit, the first network element switches from a light receiving state for receiving encoded light pulses from the allocation unit into a radio transmission state for transmitting the encoded ID, and the second network element switches from a light receiving state for receiving encoded light pulses from the allocation unit into a radio receiving state for receiving the encoded ID.

5. The method as claimed in claim 1, further including:
with the allocation unit, receiving the encoded ID from the first network element and transmitting it to the second network element.

6. The method as claimed in claim 1, further including:
with the allocation unit, transmitting a second code which causes the first network element to leave the wireless network of the second network element.

7. The method as claimed in claim 6, wherein the second code for removing network elements from the wireless network is the first code transmitted over a longer time period or a number of times.

8. The method as claimed in claim 1, wherein the second network element has a network administration function and further including:

with the allocation unit, transmitting a second code which causes the second network element to break up the wireless network.

9. The method as claimed in claim 8, wherein the second code for breaking up the wireless network is the first code transmitted over a longer time period or a number of times.

10. A system for allocating network element to a wireless network comprising:

an allocation unit including a transmitter configured to transmit, in a user-controlled manner, a code to a first network element, the first network element being configured to transmit in response to receiving the code an encoded identification (ID) comprising its ID and the received code, a second network element having network administration function and being configured to allocate the first network element to its wireless network in response to receiving the encoded ID from the first network element, wherein the second network element is configured to be activated for a predetermined time to receive the encoded ID from the first network element by receiving the code from the allocation unit, wherein the second network element is configured to accept only identifications from network elements having the same code, and wherein the allocation unit is one of a plurality of differently encoded allocation units, said allocation unit having a short transmission range transmitter configured to send out a code that is unique for each allocation unit.

11. The system as claimed in claim 10, wherein the transmitter is configured to transmit an encoded light pulse and an encoded radio signal.

12. The system as claimed in claim 10, further including: a receiver configured to receive encoded IDs.

13. The system as claimed in claim 10, further including: one or more devices for displaying the respective operating state.

14. The system as claimed in claim 10, wherein the transmitter is configured to transmit, in a user-controlled manner, a second code which causes the first network element to leave the wireless network of the second network element or which causes the second network element to break up the wireless network.

* * * * *